(12) United States Patent
Plummer (10) Patent No.: US 11,320,349 B2
(45) Date of Patent: May 3, 2022

(54) SPHEROID TISSUE MICROARRAY AND METHODS OF MANUFACTURE

(71) Applicant: Micromatrices Associates Ltd., Fife (GB)

(72) Inventor: Simon M. Plummer, Fife (GB)

(73) Assignee: MICROMATRICES ASSOCIATES LTD., Fife (GB)

( * ) Notice: Subject to any disclaimer, the term of this patent is extended or adjusted under 35 U.S.C. 154(b) by 785 days.

(21) Appl. No.: 16/091,769

(22) PCT Filed: Dec. 9, 2016

(86) PCT No.: PCT/GB2016/053907
§ 371 (c)(1),
(2) Date: Oct. 5, 2018

(87) PCT Pub. No.: WO2017/174955
PCT Pub. Date: Oct. 12, 2017

(65) Prior Publication Data
US 2019/0162637 A1 May 30, 2019

Related U.S. Application Data

(60) Provisional application No. 62/390,660, filed on Apr. 6, 2016.

(30) Foreign Application Priority Data

Sep. 13, 2016 (GB) ...................................... 1615517

(51) Int. Cl.
| | |
|---|---|
| G01N 1/36 | (2006.01) |
| C12M 1/32 | (2006.01) |
| C12N 5/071 | (2010.01) |
| G01N 1/31 | (2006.01) |
| C12N 5/0793 | (2010.01) |
| C12N 5/09 | (2010.01) |
| C12M 1/12 | (2006.01) |
| C12N 5/00 | (2006.01) |
| C12M 3/00 | (2006.01) |
| G01N 1/28 | (2006.01) |
| G01N 1/00 | (2006.01) |

(52) U.S. Cl.
CPC ............... *G01N 1/36* (2013.01); *C12M 21/08* (2013.01); *C12M 23/04* (2013.01); *C12M 23/12* (2013.01); *C12N 5/0062* (2013.01); *C12N 5/0068* (2013.01); *C12N 5/0075* (2013.01); *C12N 5/067* (2013.01); *C12N 5/0619* (2013.01); *C12N 5/0625* (2013.01); *C12N 5/0693* (2013.01); *G01N 1/2806* (2013.01); *G01N 1/312* (2013.01); *C12N 2513/00* (2013.01); *C12N 2533/76* (2013.01); *C12N 2535/00* (2013.01); *G01N 2001/002* (2013.01); *G01N 2001/362* (2013.01); *G01N 2001/364* (2013.01); *G01N 2001/366* (2013.01); *G01N 2001/368* (2013.01)

(58) Field of Classification Search
None
See application file for complete search history.

(56) References Cited

U.S. PATENT DOCUMENTS

| | | | |
|---|---|---|---|
| 2010/0323907 A1 | 12/2010 | Ton-That et al. | |
| 2011/0171712 A1 | 7/2011 | Rivron et al. | |

(Continued)

FOREIGN PATENT DOCUMENTS

| | | | |
|---|---|---|---|
| EP | 1921450 A1 | 5/2008 | |
| JP | 2009-524414 A | 7/2009 | |
| WO | 2004111614 A1 | 12/2004 | |

(Continued)

OTHER PUBLICATIONS

Mehesz et al., "Scalable robotic biofabrication of tissue spheroids," Biofabrication (May 12, 2011); 3(2):025002 (8 pages).

(Continued)

*Primary Examiner* — Teresa E Knight
(74) *Attorney, Agent, or Firm* — Fox Rothschild LLP (57) ABSTRACT

A spheroid tissue microarray comprises an array of tissue spheroids embedded within a porous mold. The product may be impregnated with a wax or resin and sectioned, and contains spheroids which are precisely located in a regular geometric grid. A method of manufacturing a spheroid tissue microarray comprises the steps of: forming a mold of porous material from liquid mold material in a casting mold, and allowing the liquid mold material to set; removing the porous mold from the casting mold; topping up the porous mold with further liquid mold material, and allowing recesses to form in the surface of the mold by the drawing-in of liquid mold material through shrinkage as the liquid mold material sets; placing tissue spheroids into the recesses in the surface of the porous mold; and sealing the tissue spheroids within the mold by topping off with liquid mold material and allowing the liquid mold material to set. An alternative method comprises the steps of: forming a mold of porous material from liquid mold material in a casting mold; allowing the liquid mold material to set; removing the porous mold from the casting mold; placing spheroids in recesses at the bases of wells in the mold of porous material; and sealing the spheroids within the porous mold by adding further porous material on top of the spheroids; wherein the recesses at the bases of the wells in the porous material are formed by protrusions of the casting mold carrying further, nipple-shaped, protrusions.

35 Claims, 7 Drawing Sheets

(56) References Cited

U.S. PATENT DOCUMENTS

2012/0015440 A1    1/2012  Otsuka et al.
2014/0106452 A1    4/2014  Vukasinovic

FOREIGN PATENT DOCUMENTS

WO    2009116951 A2    9/2009
WO    2012131000 A1    10/2012
WO    2015069742 A1    5/2015

OTHER PUBLICATIONS

Gong et al., "Generation of Multicellular Tumor Spheroids with Microwell-Based Agarose Scaffolds for Drug Testing," PLOS ONE (Jun. 19, 2015); 10(6):e0130348 (18 pages).

Hardelauf et al., "Microarrays for the scalable production of uniform and metabolically relevant tumour spheroids," 14th International Conference on Miniaturized Systems for Chemistry and Life Sciences, Groningen, the Netherlands (Oct. 3-7, 2010): pp. 2023-2025.

Fukuda, et al: "Micromolding of Photocrosslinkable Chitosan Hydrogel for Spheroid Microarray and Co-Cultures", Biomaterials, 2006, vol. 27, pp. 5259-5267.

Tumour cell spheroids ~500μM diam
~100x5μM sections

Scale in mm
Tumour spheroid array showing size of the tumour spheroids

FIG. 2A

Scanned image of the spheroid array section stained with haematoxylin and eosin

FIG. 2B

Zoomed high resolution image of a single spheroid in the array

FIG. 2C

Neuronal spheroids ~500μM diam

Polystyrene Bead 'spheroid' ~500μM diam

Neuronal spheroid array showing size of the neuronal spheroids

FIG. 3A

Scanned image of the spheroid array section stained with haematoxylin and eosin

Zoomed high resolution image of a single spheroid in the array

FIG. 3C

Incorporation of polystyrene beads
into block showing block

FIG. 4A

Section of the polystyrene beads

FIG. 4B

Features:
- Planar arrangement of spheroids in a block.
- Geometric grid suitable for automated image analysis.
- Retains 96 wells format/organisation Liver spheroid

FIG. 5A

Tumour spheroid

SPHEROID TISSUE MICROARRAY AND METHODS OF MANUFACTURE

The present invention relates to a spheroid tissue microarray, and methods of manufacturing the same.

Automated high throughput techniques are used in biological sciences to perform simultaneous multiple experiments for large scale repetition. In this way, methods which are normally performed individually can be performed in large numbers simultaneously without impacting on their quality.

In the biological sciences, a microarray is an array of a large number of biological materials on a solid substrate, for example a glass slide or thin film, by which the biological materials can be assayed using high throughput screening. Various different types of microarray are known, including DNA microarrays, protein and peptide microarrays, antibody microarrays and tissue microarrays.

Tissue microarrays are known which comprise paraffin blocks in which a large number (e.g. up to 1000) of separate tissue samples can be assembled in an array to allow multiplex histological analysis. In conventional techniques, a hollow needle is used to remove small (<1 mm) tissue samples from materials of interest, which are inserted into a paraffin block in a precisely spaced array. Sections from the block may be cut, for example, using a microtome, and histologically analysed. Each microarray block can be cut into many sections (e.g. 100-500), which can be independently tested.

WO 2015/069742 discloses preparing a mold having an array of wells, which are prefilled with water. Spheroids are pipetted into the water-filled wells and the water and spheroids within the wells are then infused with agarose. Once the agarose is set, it is removed from the mold. The implication is that the spheroids are at the base of downwardly extending agarose members, rather than embedded within the body of the agarose. The efficiency with which spheroids are retained at the base of the agarose members upon removal from the mold is unclear. The mold may be made from plastic or silicone. This document teaches that the spheroids are on the same plane so that they can be sectioned and stained on one slide. However, this document does not disclose precise horizontal positioning of the spheroids; instead it merely discloses that the spheroids are within separate compartments.

The present invention seeks to provide an improved spheroid tissue microarray, and methods of manufacturing the same. Herein the term "spheroid" is intended to mean agglomerates of cells, for example organoids, or spherical agglomerates of cells in a tissue-like structure. The skilled person will understand that such structures do not need to be strictly spherical; rather they have a three dimensionality reflective of in vivo properties.

According to the present invention there is thus provided a spheroid tissue microarray comprising an array of tissue spheroids embedded within a porous mold.

The spheroid tissue microarray is suitable for use in high-throughput tissue histology. The microarray enables the substantially planar alignment, positioning and embedding of tissue spheroids in a geometric grid, allowing the simultaneous sectioning of a large number (for example, hundreds) or individual spheroids for subsequent histological analysis, for example staining, transcriptomic/proteomic profiling and image analysis. However, the spheroid tissue microarray is suitable for use in other fields, for example in tissue testing in the personal care and cosmetic industries, where animal testing may not be permitted.

The spheroid tissue microarray of the present invention comprises a porous mold, i.e. a mold formed from porous material. Potentially, any suitable porous material may be used, and a preferred material is an agarose or agar gel.

It has been found that the porosity is important and beneficial; one consequence is that the whole product in a subsequent step can be impregnated with a wax, and therefore can be conveniently sectioned. Porosity throughout the product, rather than just in the vicinity of each spheroid, provides further and inventive points of distinction over some prior art documents which for example use a porous matrix but only within separately divided wells. In the present invention a mold is used which is itself porous. The present invention enables the formation of an ordered wax block which can be sectioned many times.

In contrast to the present invention, WO 2015/069742 discloses a mold made from plastic or other material rather than a mold which is porous. In the present invention the spheroids are surrounded by a porous matrix which results in greater strength and allows a higher density of spheroids per unit area.

The porous mold is initially formed to contain a series of regularly positioned holes, arranged in a grid pattern. The holes are preferably between 0.2 and 3.0 mm diameter, for example 0.5 to 1.5 mm, preferably approximately 1 mm. The holes may have a depth of between 2 and 5 mm, for example 3 to 4 mm, preferably approximately 4 mm. The mold may contain, for example, from 100 to 300 holes, such as a 10×17 grid of 170 holes. However, any number of holes may be contained in the porous mold, for example 96 holes to reflect the industry standard 96 well plate.

The spheroid tissue microarray of the present invention also comprises an array of tissue spheroids embedded within the porous mold.

The spheroids can be positioned very accurately so that the distance between them is very uniform. This is because, during the preparation of the array, the holes on which the spheroids are to be located take the form of concave wells or "dimples", meaning that each spheroid is located at the centre of each well. This contrasts with flat bottomed wells in some arrays.

In an array the intention will be that spheroids are located at predetermined ideal positions, usually at regular intervals in a regular array. Optionally, in the present invention, the spheroids have a mean diameter and are located horizontally such that their centres are no more than said mean diameter away from their predetermined ideal positions. Optionally they are no more than half of said mean diameter away, optionally no more than 0.1 of said mean diameter away.

The accurate positioning of the spheroids means that it is possible to overlay a grid or template for, amongst other things, automated image analysis. Optionally the method may be automated by the use of robotics.

Optionally the centrepoint of each spheroid is no more than 500 micrometers, optionally no more than 300 micrometers, optionally no more than 200 micrometers, optionally no more than 100 micrometers, optionally no more than 50 micrometers, optionally no more than 20 micrometers, optionally no more than 10 micrometers, from the desired horizontal location.

Optionally, where the spheroids are arranged substantially in a regular geometric (e.g. square) array, and where the distance between adjacent spheroids is x, the standard deviation of spheroid positioning away from the ideal grid spheroid locations is no greater than 0.5x, optionally no greater than 0.25x, optionally no greater than 0.2x, optionally no greater than 0.1×, optionally no greater than 0.05×, or optionally no greater than 0.02×.

The density of spheroids on the array can be very high, for example 100 spheroids per $cm^2$ or more, for example 200 spheroids per $cm^2$ or more, for example 400 spheroids per $cm^2$ or more, for example 500 spheroids per $cm^2$ or more, for example up to 1000 spheroids per $cm^2$. Robotic apparatus and/or process steps as described below may be used to achieve the highest levels of precision.

The tissue spheroids may comprise any suitable tissue to be tested or assayed. For example, the tissue may be derived from induced pluripotent stem cells, primary cells or cell lines such as those derived from cancerous tissues. Thus, the tissue spheroids may be made from a range of different cell types including, for example, neuronal cells, skin cells, liver cells, tumour cells, stromal cells (e.g. fibroblasts and macrophages), immune cells (e.g. lymphocytes and T-cells), and endothelial cells (e.g. vascular endothelial cells). The tissue spheroids may be formed from the in vitro 3D culture of cells.

The spheroid tissue microarray may comprise tissue spheroids of different sizes. The tissue spheroids may have a spheroid diameter of 50 to 500 μm, for example 100 to 500 μm, such as 150 μm or/to 350 μm.

The tissue spheroids used in the spheroid tissue microarray may comprise a substrate on which cells are grown prior to embedding. For example, the substrate may be a bead formed from a suitable material, such as polystyrene or another suitable plastics material.

Tissue spheroids comprising a substrate such as a polystyrene bead may have particular utility for the growth of skin cells, for example for use in the personal care or cosmetic industries. In Europe for example, animal testing is not permitted for cosmetics, and there is thus a need for human tissue tests. Growth of human skin on beads is useful because the skin cells tend to grow on the bead as they would in nature, i.e. (where present) epidermis outermost, dermis beneath the epidermis, and hypodermis below the dermis. Studies have found that if human skin spheroids are formed without a substrate, then the skin layers tend to grow "inside-out" compared to how they form in nature, making them unsuitable for testing.

The spheroid tissue microarray may be impregnated with an additional structural agent, such as paraffin wax or resin, for additional structural stability.

The tissue spheroids may be stained for histological analysis, for example the measurement of biomarkers (biological indicator molecules) by automated image analysis. For example, cellular responses (biomarkers) may be monitored by immunostaining microscope-based imaging of cells, such as with a confocal scanner and automated image analysis. For example, haematoxylin and eosin stain is one of the principal histological stains. Staining typically occurs after the spheroid tissue microarray has been cut into sections for analysis, for example by a microtome.

According to the present invention there is also provided a method of manufacturing a spheroid tissue microarray, which method comprises the steps of: forming a mold of porous material from liquid mold material in a casting mold, and allowing the liquid mold material to set; removing the porous mold from the casting mold; topping up the porous mold with further liquid mold material, and allowing recesses to form in the surface of the mold by the drawing-in of liquid mold material through shrinkage as the liquid mold material sets; placing tissue spheroids into the recesses in the surface of the porous mold; and, sealing the tissue spheroids within the mold by topping off with liquid mold material and allowing the liquid mold material to set.

This method of the present invention preferably manufactures a spheroid tissue microarray according to the present invention.

The method thus comprises the step of forming a mold of porous material from liquid mold material in a casting mold. The temperature at which the porous material will be liquid will depend upon the material being used. A preferred porous mold material is 0.5-4% agarose in water, preferably a 2% agarose/water mixture. For this material, a casting temperature of from 60 to 70° C. is suitable. The casting mold is preferably pre-equilibrated to a suitable temperature, for example 70° C. for liquid agarose gel. The casting mold may be topped off with liquid mold material, for example using a tissue cassette case.

The liquid mold material is allowed to set in the casting mold. A suitable time period and temperature for this will depend upon the material being used. For the preferred agarose gel used in the present invention, suitable setting conditions are room temperature for 20 to 45 minutes, preferably approximately 30 minutes, followed by chilling at 0 to 5° C. (e.g. 4° C.) for 20 to 45 minutes (e.g. 30 minutes).

The porous mold is then removed from the casting mold. This must be achieved without fracturing the porous mold, and may be assisted by stiffening the porous mold, for example by chilling. Thus, an agarose gel mold may be stiffened for removal from the casting mold by chilling at a temperature of, for example, −20° C. for an appropriate time period (e.g. 5 to 15 minutes).

The removal of the porous mold from the casting mold may also be facilitated by using a silicon, glycerol or polytetrafluoroethylene (teflon) material, or other hydrophobic material, on the casting mold, e.g. a silicon, glycerol or teflon spray.

Once removed from the casting mold, the porous mold is topped up with further liquid mold material, and recesses allowed to form in the surface of the mold by the drawing-in of liquid mold material through shrinkage as the liquid mold material sets. Prior to topping up, the porous mold may be heated to remove trapped gasses or other impurities, at a suitable temperature, for example 60 to 70° C., for a suitable period of time, for example 10 to 30 minutes (e.g. 20 minutes). This heating is preferably performed in a sealed environment to prevent evaporation of material. The porous mold is topped up with liquid mold material as described hereinabove. The liquid mold material may be the same or different to the material used to form the porous mold; for example, an agarose gel at 0.1-1.0% in water, optionally 0.4% in water or 0.7% in water, may be used. A suitable dye marker may be added to the topping-up liquid mold material, for example bromophenol blue or coomassie blue. As the liquid material is allowed to set it is drawn into the porous mold under surface tension forming recesses in the surface of the mold, due to shrinkage of the mold material as it sets. The recesses are typically formed within the top 1 mm of the mold.

Tissue spheroids are placed into the recesses in the surface of the porous mold, and sealed within the mold by topping off with further liquid mold material. Again, for agarose gel in water, a temperature of from 60 to 70° C. is suitable. The liquid mold material is then allowed to set, for example by cooling down to 0 to 5° C. (e.g. 4° C.) for 30 minutes.

The casting mold can be made from a variety of materials such as silicone or polycarbonate. The casting mold is generally inert and non-porous. Protrusions of the casting mold are used to make complementary wells in the agarose/porous mold and can be varied in their shape, dimension and spacing.

In methods as described above, after the porous (e.g. agarose) mold is released from the casting mold, further porous (e.g. agarose) material is added to wells in the porous (e.g. agarose) mold, and then recesses form on the further porous (e.g. agarose) material as it is drawn into the wells, and subsequently spheroids are placed in those recesses.

An alternative way of providing suitable recesses for the spheroids is as follows. The protrusions of the casting mold (e.g. U-shaped protrusions) may have smaller protrusions (e.g. nipple-shaped protrusions) on their tops. These result in wells (e.g. U-shaped wells) in the porous (e.g. agarose) mold with recesses (e.g. dimples) at their bases (e.g. at their centre points) that allow the spheroids to be positioned under gravity precisely in the dimples of the wells and retain them when the wells are subsequently filled with porous material (e.g. agarose). Thus, in this variation of the method, precision is achieved by having dimples or recesses which are formed on the porous mold base itself rather than on additional porous material. Different ways of achieving high levels of spheroid location precision expand the applicability of the invention and the automation possibilities.

Thus, from a further aspect the present invention provides a method of manufacturing a spheroid tissue microarray, which method comprises the steps of: forming a mold of porous material from liquid mold material in a casting mold; allowing the liquid mold material to set; removing the porous mold from the casting mold; placing spheroids in recesses at the bases of wells in the mold of porous material; and sealing the spheroids within the porous mold by adding further porous material on top of the spheroids; wherein the recesses at the bases of the wells in the porous material are formed by protrusions of the casting mold carrying further, nipple-shaped, protrusions.

Optional and/or preferred features of the first method of the present invention also apply where appropriate, mutatis mutandis, to the alternative method of manufacture.

The methods of the present invention thus result in spheroids being sandwiched between porous matrix components (e.g. between agarose layers). This is because the spheroids are placed onto a porous substrate (e.g. agarose) and then further porous substrate (e.g. a different agarose material) is placed on top. In contrast, in some prior art arrays, samples are placed at the bottom of non-porous wells, so that any porous matrix goes around but not underneath the samples.

The spheroid tissue microarray formed by these methods may then be impregnated with an additional structural agent, such as paraffin wax or resin (e.g. methacrylate resin), for additional structural stability, in one or more cycles under suitable conditions. For example, paraffin wax may be impregnated into a spheroid tissue microarray formed from agarose gel in cycles of one hour at 60° C., under atmospheric pressure or lower pressure (for example 0.5 atm).

The impregnation of the mold with resin e.g. polymeric material, e.g. methacrylate polymer, allows for sectioning of the block on a microtome using for example a glass or diamond blade. Resin is more rigid than wax and allows for the cutting of thinner sections (for example, <1 uM). The sections are also more rigid and less likely than wax to distort when mounting for analysis. This allows further possibilities for achieving high levels of precision which in turn facilitates the manufacture of high density spheroid microarrays.

In use, the spheroid tissue microarray of the present invention may be sectioned, and used for analysis. For example, the sections may be placed on a glass microscope slide, and may be stained with a histological staining material, for image analysis.

The present invention provides a step forwards in terms of imaging. Several known imaging methods are "whole mount" methods, i.e. they try to image whole spheroids, and suffer in terms of diffraction, and also are unable to assay multiple endpoints due to inability to apply heat induced retrieval (HIER) of the targets in whole mount preparations. The present invention is advantageous in avoiding light scattering, providing higher resolution, and enabling more accurate analysis because it facilitates imaging throughout the spheroid. Novel applications include multiplex staining of liver spheroids with inflammatory cell markers and the quantification of drug induced liver injury using cytokine markers. Other applications include screening for drugs that act against tumours in hybrid spheroids that contain both tumour and normal cells; this can involve identification of the tumour cells through staining with a tumour specific marker such as a green fluorescent (GF) tagged protein and subsequently staining for the drug target within the tumour cells.

Embodiments of the present invention will now be described in detail with reference to the accompanying drawings, in which:

FIG. 4b shows a section of the spheroid tissue microarray shown in FIG. 4a;

With reference to FIGS. 1a to 1d, a preferred method of manufacturing a spheroid tissue microarray of the present invention is described.

Figure 1A:
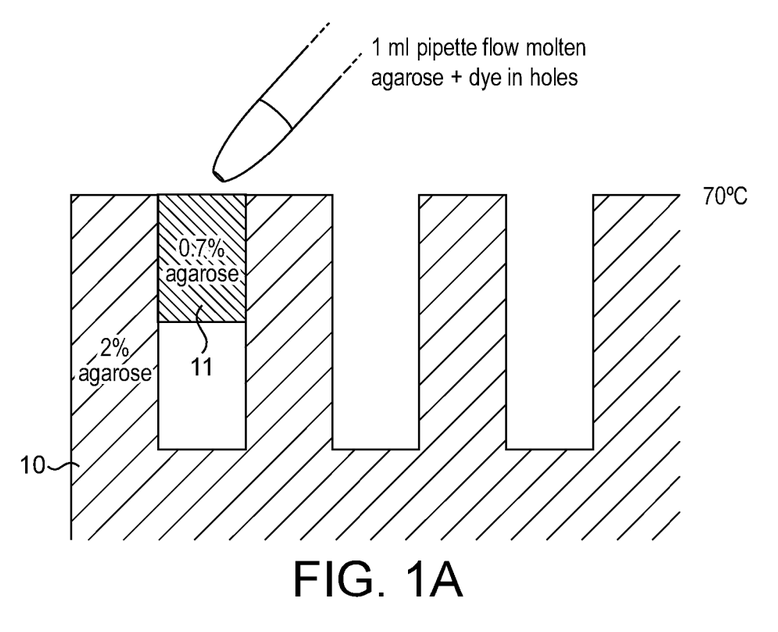
FIGS. 1a to 1d illustrate a method of manufacturing a spheroid tissue microarray according to an embodiment of the present invention.

In a preferred method, the porous mold is made by pouring liquid gel material into a casting mold. Any suitable porous material, preferably an agarose or agar gel material, may be used to form the porous mold. A preferred agarose gel composition comprises 0.5 to 4% agarose in water, preferably a 2% agarose/water mixture. The liquid gel agarose is poured into the casting mold at a temperature of 60 to 70° C., the casting mold being pre-equilibrated at 70° C. A tissue cassette case (for example, of acetal polymer) is placed on top of the casting mold and topped up with liquid gel agarose. The liquid gel agarose is allowed to set at room temperature for a minimum of 20 to 45 minutes, preferably 30 minutes, and is then chilled at 4° C. for 30 minutes. The gel is then chilled at a temperature of −20° C. for 10 minutes to stiffen the gel, so it can be removed from the casting mold without fracturing. The porous mold may be removed from the casting mold by inserting two micro spatulas (width 4 mm, depth 0.5 mm, length 10 cm) down each side of the base of the casting mold and levering the porous mold out of the casting mold.

The porous agarose mold is then heated in an oven to 70° C. in a sealed plastic bag to prevent evaporation for 20 minutes, and holes in the mold are then filled with liquid agarose gel at 0.1 to 1.0% in water, preferably 0.4%, containing coomassie blue dye marker, at a temperature from 60 to 70° C., preferably 70° C. The liquid agarose gel is drawn into the mold under surface tension and is allowed to set forming recessed chambers in the top 1 mm of the mold that occur due to shrinkage of the gel volume as it sets (see FIG. 1a).

Figure 1B:
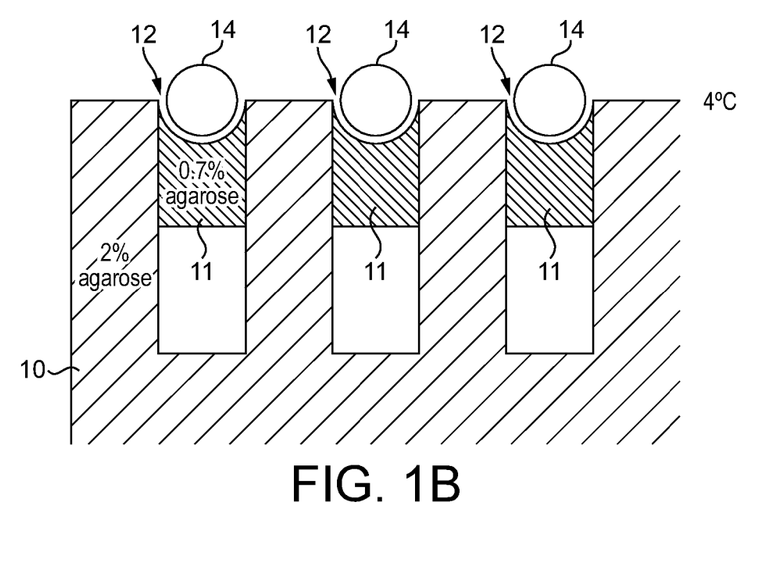
Figure 1C:
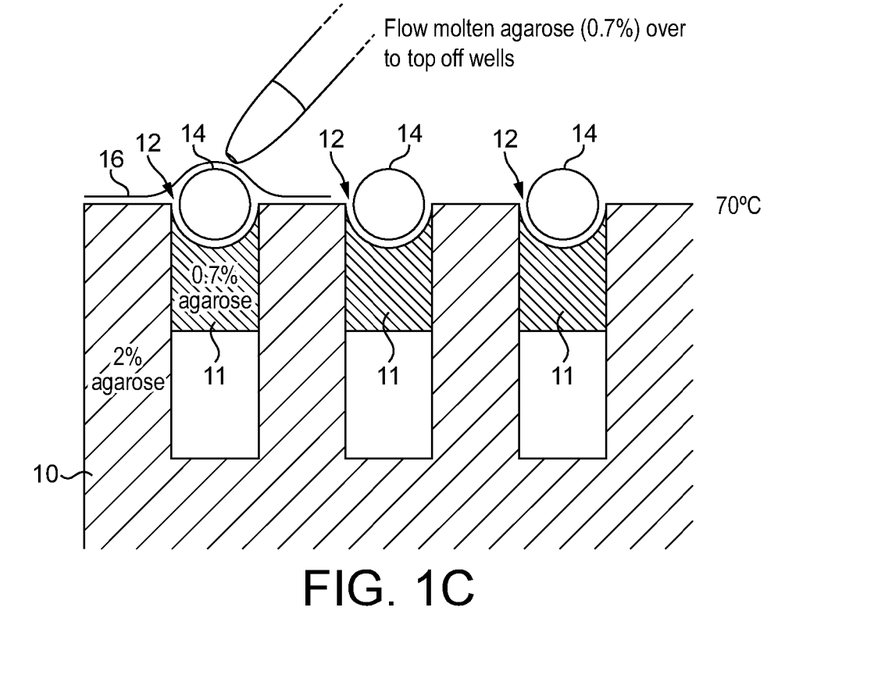

Tissue spheroids of a diameter of from 50 to 500 μm, for example 100 to 500 μm, such as 150 μm or/to 350 μm, which may be formed from the in vitro 3D culture of cells, and which may be derived from induced pluripotent stem cells, primary cells or cell lines such as those derived from cancerous tissues, are fixed in neutral buffered formaldehyde (NBF) containing 100 ml pure formaldehyde dissolved in 900 ml deionised water containing 4 g of sodium dihydrogen phosphate, monohydrate and 6.5 g disodium hydrogen phosphate, and then placed in the recesses at the top of the agarose mold (see FIG. 1b).

After the tissue spheroids are placed in the agarose mold recesses they are sealed in by topping off with liquid agarose gel at a temperature from 60 to 70° C. (see FIG. 1c). The mold is then cooled at 4° C. for 30 minutes to set the agarose gel seal, and placed in a solution of 70% ethanol for a minimum of 1 to 10 days, preferably 5 days.

Figure 1D:
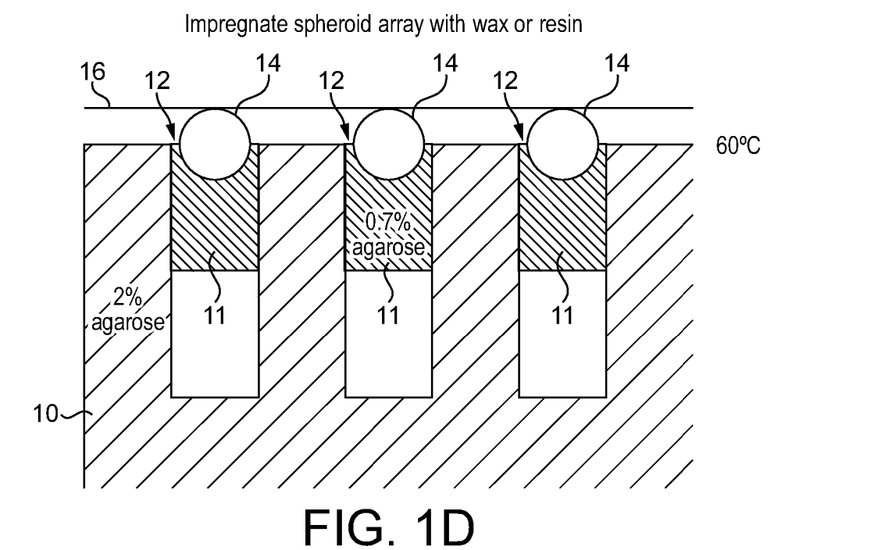
Figure 2A:
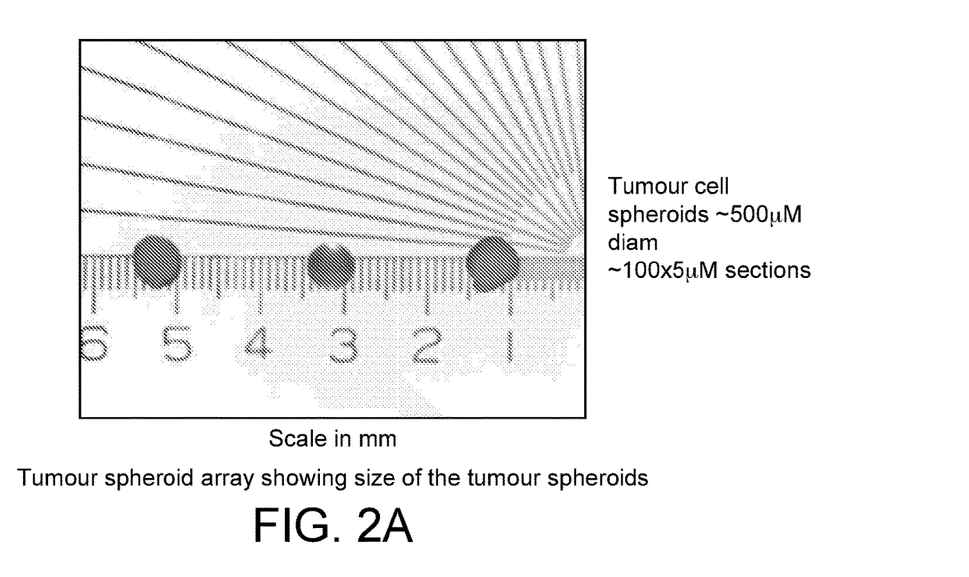
FIG. 2a shows a tumour spheroid array according to an embodiment of the present invention, showing the size of the tumour spheroids.
Figure 2B:
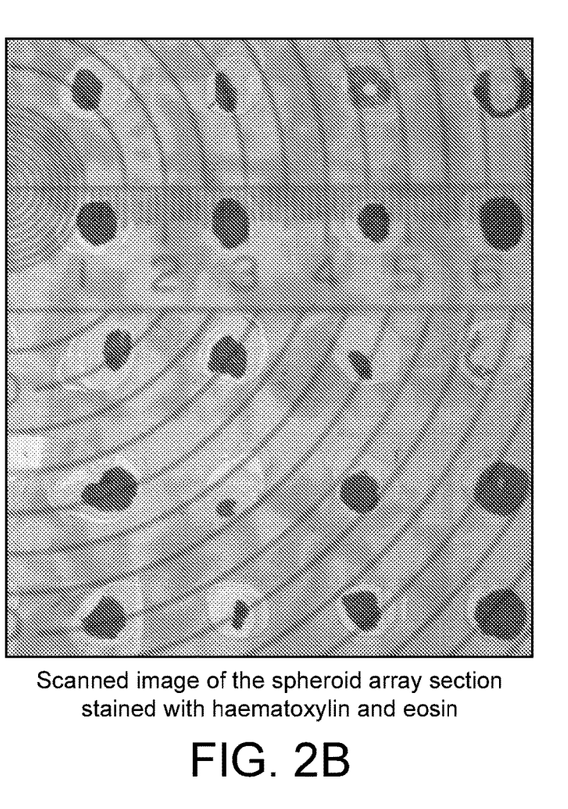
FIG. 2b is a scanned image of the spheroid array section of the tumour spheroid array shown in FIG. 2a stained with haematoxylin and eosin.
Figure 2C:
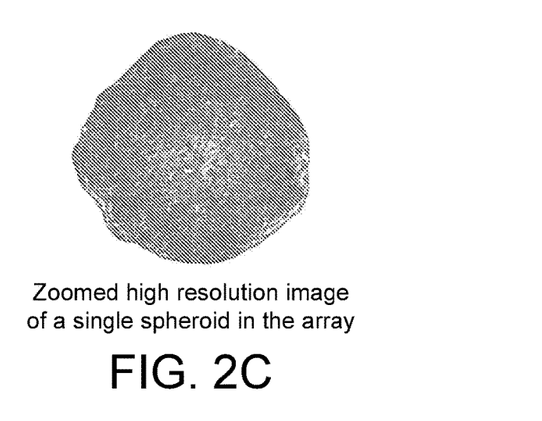
FIG. 2c is a zoomed high resolution image of a single spheroid in the array shown in FIGS. 2a and 2b.
Figure 3A:
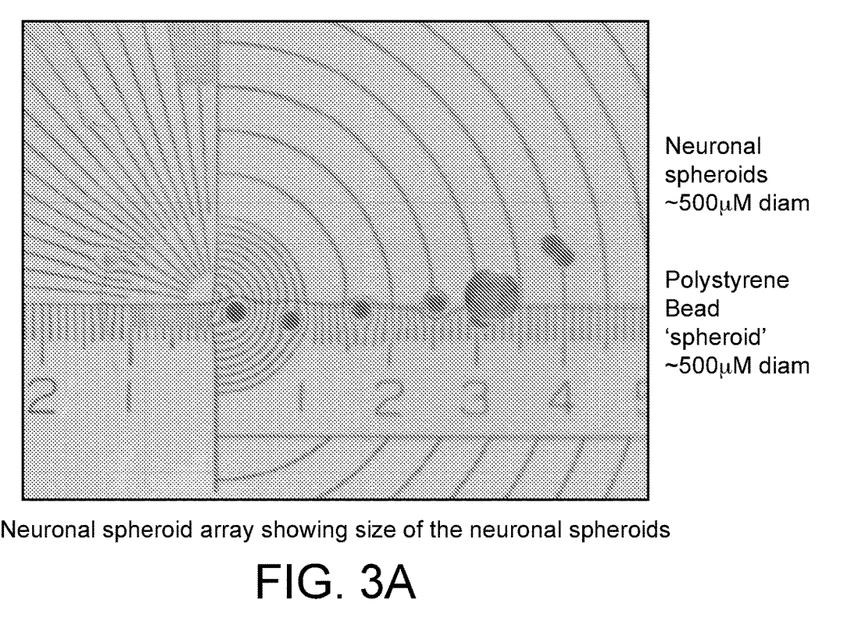
FIG. 3a shows a neuronal spheroid array according to an embodiment of the present invention showing the size of the neuronal spheroids.
Figure 3B:
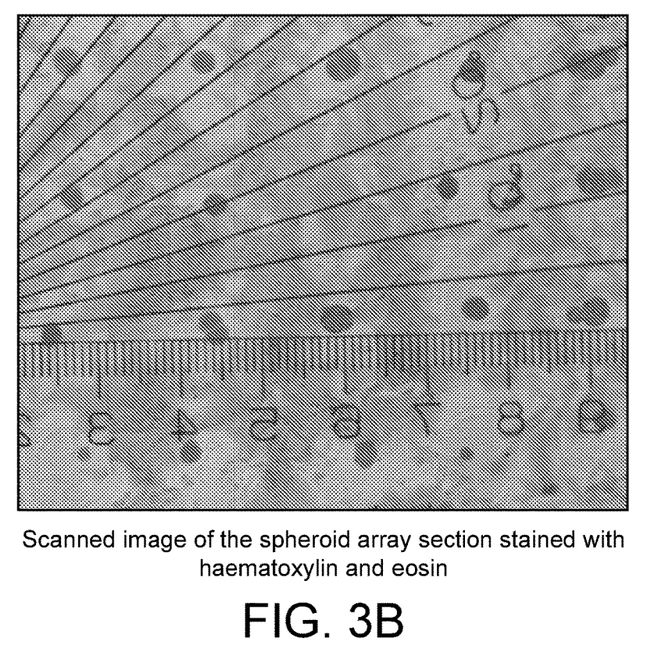
FIG. 3b is a scanned image of the spheroid array section of the neuronal spheroid array shown in FIG. 3a stained with haematoxylin and eosin.
Figure 3C:
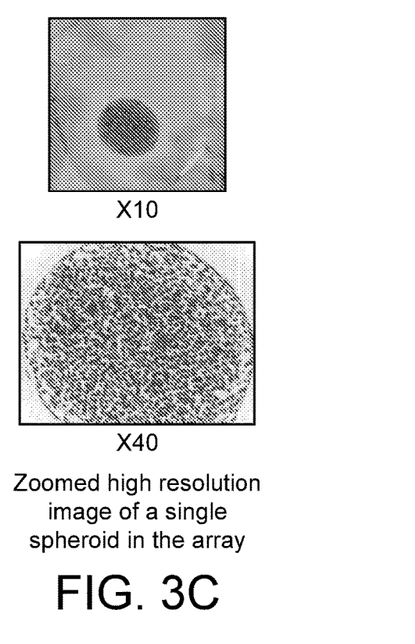
FIG. 3c is a zoomed high resolution image of a single spheroid in the array shown in FIGS. 3a and 3b.
Figure 4A:
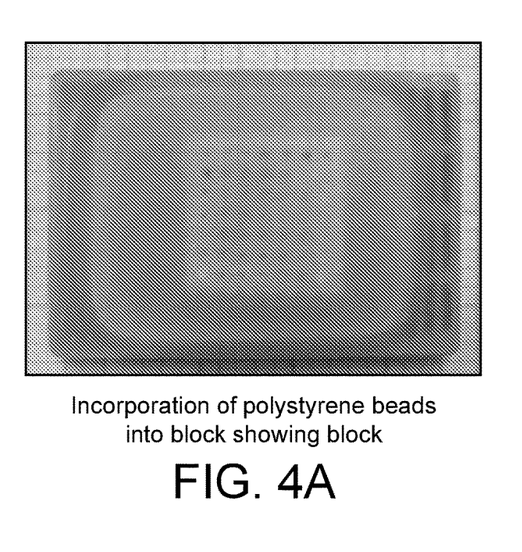
FIG. 4a shows a spheroid tissue microarray according to an embodiment of the present invention incorporating polystyrene beads.
Figure 4B:
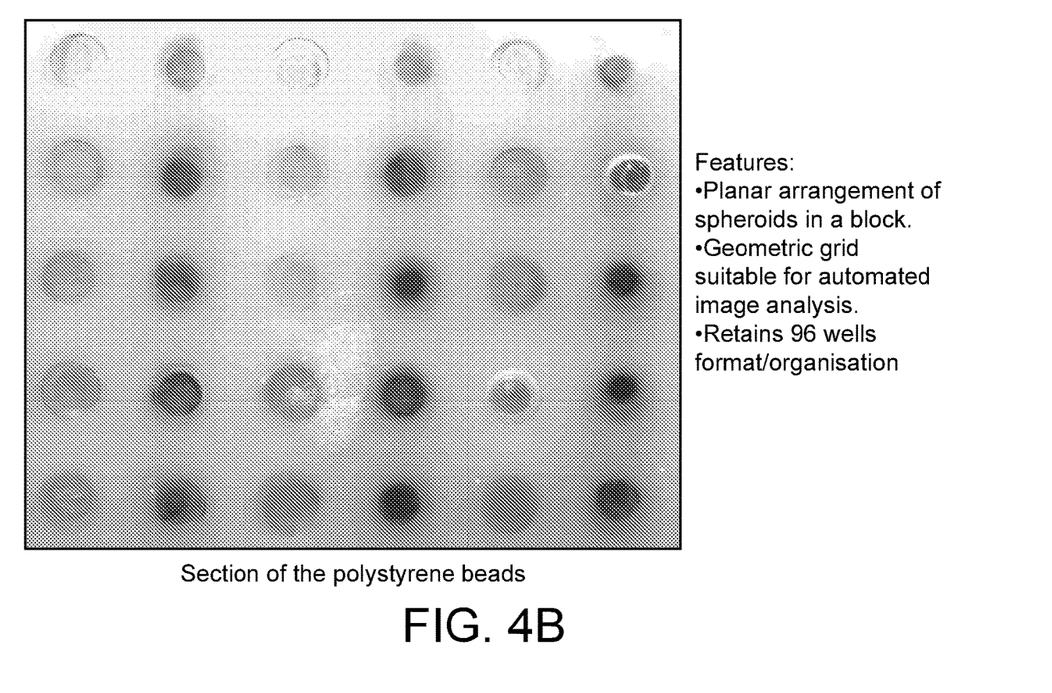
Figure 5A:
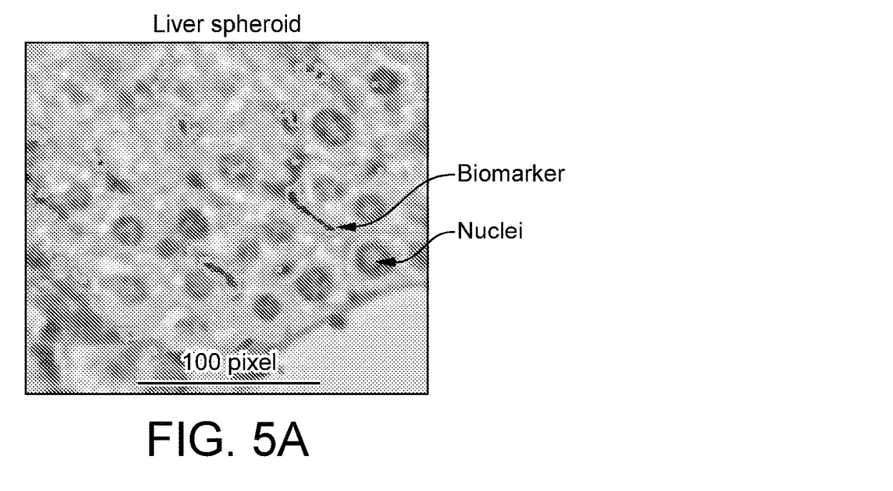
FIG. 5a shows a high resolution image of a tumour cell spheroid from a spheroid tissue array according to an embodiment of the present invention.
Figure 5B:
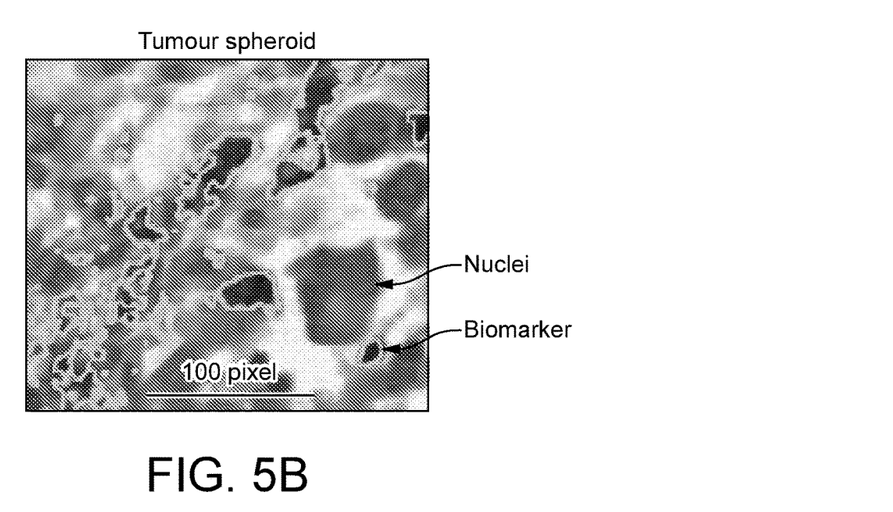
FIG. 5b shows a high resolution image of a tumour spheroid.
Figure 5C:
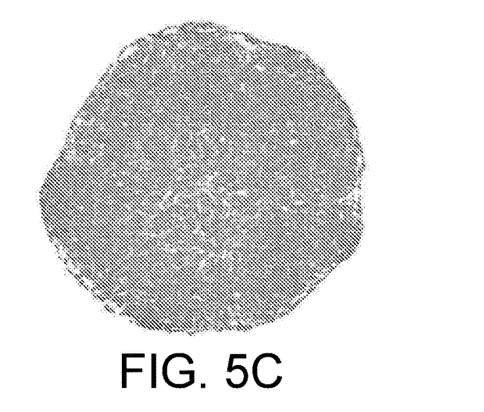
FIG. 5c shows an automated image analysis of a whole spheroid section across all spheroids in a spheroid tissue microarray according to an embodiment of the present invention.

The spheroid tissue microarray is then impregnated with molten paraffin wax in a tissue processor (FIG. 1d), using the following cycles:

| Time (hours) | Solution | Temp (° C.) | Vacuum (in Hg) |
| --- | --- | --- | --- |
| 2 | 70% ethanol | 25 | — |
| 2 | 95% ethanol | 25 | — |
| 2 | 100% ethanol | 25 | — |
| 2 | 100% ethanol | 25 | — |
| 2 | 100% ethanol | 25 | — |
| 1 | Xylene | 25 | — |
| 2 | Xylene | 25 | — |
| 2 | Xylene | 25 | — |
| 3 | Paraffin | 60 | — |
| 3 | Paraffin | 60 | 15 |

After paraffin embedding, the spheroid tissue microarray may be sectioned and the sections placed on glass microscope slides (25 mm×75 mm), prior to histological staining and/or matrix assisted laser desorption imaging mass spectrometric proteomic profiling and automated image analysis.

Examples of the images available from different spheroid tissue microarrays of embodiments of the present invention are shown in FIGS. 2a through 5c.

Figure 6:
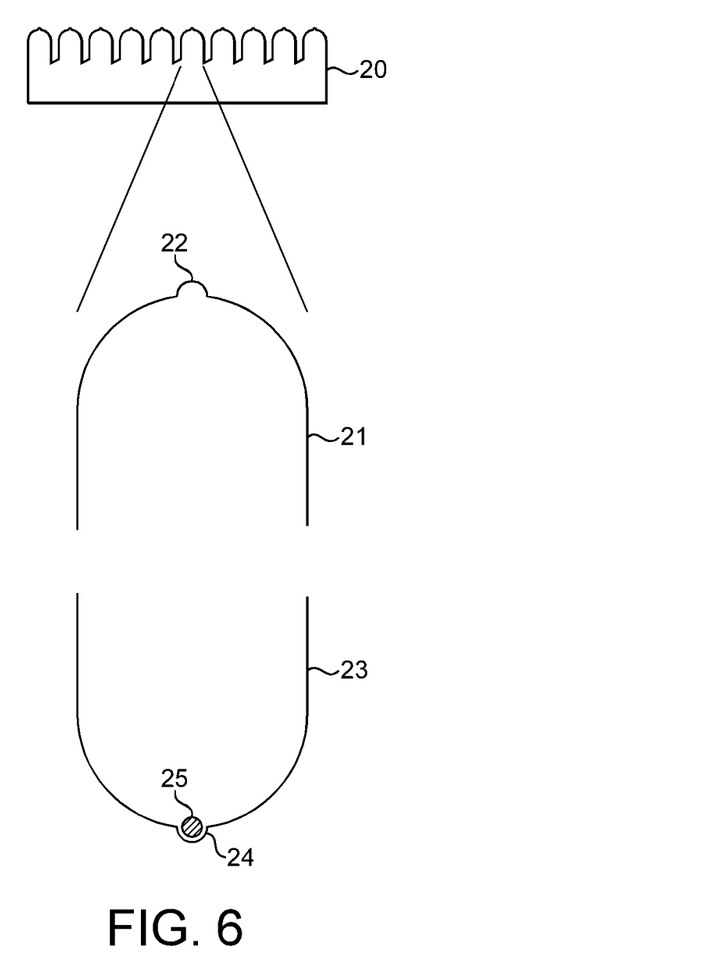
FIG. 6 shows the structure of wells formed in a porous mold according to an alternative method of the present invention.

Whereas FIG. 1 illustrates one method of locating spheroids in an array, FIG. 6 illustrates an alternative method. With reference to FIG. 6, casting mold 20, shown in cross-section, contains protrusions 21, shown in enlarged form, which are generally U-shaped but have smaller, nipple-shaped protrusions 22. These result in a porous mold (e.g. an agarose mold) which has U-shaped wells 23 with dimples 24 at the base of the wells 23, for location of spheroids 25.

The spheroids within the products of the present invention have been shown to maintain their integrity. This has been confirmed using cellular morphological analysis verified by a pathologist.

The present invention can thus provide a spheroid tissue microarray and method of manufacturing the same, for use in high throughput histology. The spheroid tissue microarray provides the planar alignment and positioning of tissue spheroids on a geometric grid facilitating simultaneous sectioning of many (e.g. hundreds) of individual spheroids for subsequent analysis.

The invention claimed is:

1. A spheroid tissue microarray comprising a regular array of tissue spheroids arranged in a grid pattern and embedded within a porous mold, wherein the spheroids are horizontally accurately positioned such that the centrepoint of each spheroid is no more than 100 micrometres from its regular grid location.

2. The spheroid tissue microarray according to claim 1 wherein the porous mold is formed from an agarose or agar gel.

3. The spheroid tissue microarray according to claim 1 which is formed to contain a series of regularly positioned holes arranged in the grid pattern.

4. The spheroid tissue microarray according to claim 3 wherein the holes have a depth of between 2 and 5 mm.

5. The spheroid tissue microarray according to claim 3 wherein the porous mold contains from 100 to 300 holes.

6. The spheroid tissue microarray according to claim 3 wherein the holes are between 0.2 and 3.0 mm diameter.

7. The spheroid tissue microarray according to claim 1 wherein the spheroids are horizontally arranged substantially in a regular square array such that the centrepoint of each spheroid is no more than 100 micrometers from its desired ideal horizontal location.

8. The spheroid tissue microarray according to claim 1 wherein the density of spheroids per $cm^2$ is between 100 and 500.

9. The spheroid tissue microarray according to claim 1 wherein the tissue spheroids comprise tissue derived from at least one consisting of the group of: induced pluripotent stem cells, primary cells, cell lines derived from cancerous tissues, neuronal cells, skin cells, liver cells, tumour cells, stromal cells, immune cells, and endothelial cells.

10. The spheroid tissue microarray according to claim 1 wherein the tissue spheroids are formed from in vitro 3D culture of cells.

11. The spheroid tissue microarray according to claim 1 wherein the tissue spheroids have a diameter of 50 to 500 μm.

12. The spheroid tissue microarray according to claim 1 wherein the tissue spheroids comprise a substrate on which cells are grown prior to embedding.

13. The spheroid tissue microarray according to claim 12 wherein the substrate is a bead formed from polystyrene (amberlite) or another porous plastic material.

14. The spheroid tissue microarray according to claim 12 wherein the tissue spheroids comprise human skin cells.

15. The spheroid tissue microarray according to claim 1 wherein the tissue spheroids are stained for histological analysis.

16. The spheroid tissue microarray according to claim 1 which is impregnated with paraffin wax or a resin.

17. A method of manufacturing a spheroid tissue microarray according to claim 1, which method comprises the steps of:
forming a mold of porous material from liquid mold material in a casting mold, and allowing the liquid mold material to set;
removing the porous mold from the casting mold;
topping up the porous mold with further liquid mold material, and allowing recesses to form in the surface of the mold by the drawing-in of liquid mold material through shrinkage as the liquid mold material sets;
placing tissue spheroids into the recesses in the surface of the porous mold; and
sealing the tissue spheroids within the mold by topping off with liquid mold material and allowing the liquid mold material to set.

18. The method according to claim 17 wherein the liquid mold material is 0.5 to 4% agarose in water.

19. The method according to claim 18 wherein the liquid mold material is a 2% agarose/water mixture.

20. The method according to claim 17 wherein the step of forming the mold of porous material from liquid mold material in a casting mold is performed at a temperature of from 60 to 70° C.

21. The method according to claim 17 wherein the casting mold is pre-equilibrated to 70° C.

22. The method according to claim 17 wherein the liquid mold material is allowed to set in the casting mold at room temperature for 20 to 45 minutes, followed by chilling at 0 to 5° C. for 20 to 45 minutes.

23. The method according to claim 17 wherein the porous mold is stiffened for removal from the casting mold by chilling at a temperature of approximately −20° C. for 5 to 15 minutes.

24. The method according to claim 17 wherein prior to topping up, the porous mold is heated at 60 to 70° C. for 10 to 30 minutes in a sealed environment.

25. The method according to claim 17 wherein the porous mold is topped up with liquid mold material comprising an agarose gel at 0.1 to 1.0% in water.

26. The method according to claim 17 wherein bromophenol blue is added to the topping-up liquid mold material.

27. The method according to claim 17 wherein the recesses are formed within the top 1 mm of the mold.

28. The method according to claim 17 wherein the tissue spheroids are sealed within the mold recesses by topping off with liquid mold material at a temperature of from 60 to 70° C.

29. The method according to claim 17 wherein following sealing of the tissue spheroids within the mold recesses, the liquid mold material is allowed to set by cooling to 0 to 5° C. for approximately 30 minutes.

30. The method according to claim 17 wherein the spheroid tissue microarray is impregnated with paraffin wax or a resin.

31. The method according to claim 30 wherein the paraffin wax is impregnated into the spheroid tissue array in cycles of approximately two hours at 60° C., under atmospheric pressure or lower pressure.

32. A method of manufacturing a spheroid tissue microarray according to claim 1, which method comprises the steps of: forming a mold of porous material from liquid mold material in a casting mold; allowing the liquid mold material to set; removing the porous mold from the casting mold; placing spheroids in recesses at the bases of wells in the mold of porous material; and sealing the spheroids within the porous mold by adding further porous material on top of the spheroids; wherein the recesses at the bases of the wells in the porous material are formed by protrusions of the casting mold carrying further, nipple-shaped, protrusions.

33. The method as claimed in claim 32 further comprising a subsequent step of impregnating the microarray with an additional structural agent.

34. The method as claimed in claim 33 wherein the structural agent is paraffin wax or a resin.

35. An analytical method comprising providing a spheroid tissue microarray as claimed in claim 1, sectioning said spheroid tissue microarray so as to simultaneously section multiple spheroids, and analyzing the sections.

* * * * *